US012661220B2

(12) United States Patent
Gorman, III et al.

(10) Patent No.: US 12,661,220 B2
(45) Date of Patent: Jun. 23, 2026

(54) PLATFORMS FOR MITRAL AND/OR TRICUSPID VALVE REPLACEMENT

(71) Applicant: MAJORO CARDIAC INNOVATIONS, LLC, Marco Island, FL (US)

(72) Inventors: Joseph H. Gorman, III, Lower Gwynedd, PA (US); Robert C. Gorman, Lower Gwynedd, PA (US); Matthew J. Gillespie, Bryn Mawr, PA (US)

(73) Assignee: MAJORO CARDIAC INNOVATIONS, LLC, Marco Island, FL (US)

( * ) Notice: Subject to any disclaimer, the term of this patent is extended or adjusted under 35 U.S.C. 154(b) by 140 days.

(21) Appl. No.: 17/844,168

(22) Filed: Jun. 20, 2022

(65) Prior Publication Data

US 2022/0313424 A1 Oct. 6, 2022

Related U.S. Application Data

(63) Continuation of application No. 16/117,103, filed on Aug. 30, 2018, now Pat. No. 11,364,114, which is a
(Continued)

(51) Int. Cl.
*A61F 2/24* (2006.01)
*A61B 17/00* (2006.01)

(52) U.S. Cl.
CPC .......... *A61F 2/2409* (2013.01); *A61F 2/2418* (2013.01); *A61B 2017/00575* (2013.01);
(Continued)

(58) Field of Classification Search
None
See application file for complete search history.

(56) References Cited

U.S. PATENT DOCUMENTS

| 5,814,058 A | 9/1998 | Carlson et al. |
| 5,944,738 A | 8/1999 | Amplatz et al. |
| | (Continued) | |

FOREIGN PATENT DOCUMENTS

| EP | 1335683 A2 | 8/2003 |
| EP | 1432369 A1 | 6/2004 |
| | (Continued) | |

OTHER PUBLICATIONS

European Patent Application No. EP 12 85 9237: Supplementary Partial European Search Report dated Jul. 24, 2015.
(Continued)

*Primary Examiner* — Shaun L David
(74) *Attorney, Agent, or Firm* — MH2 Technology Law Group, LLP

(57) ABSTRACT

A mitral valve prosthesis is percutaneously and/or transapically deployed in at least two stages. In a first stage, a mitral annular ring platform adapted for percutaneous delivery is delivered to and anchored in the mitral valve annulus. In the second stage, a valved-stent mitral valve prosthetic device adapted for percutaneously delivery is delivered to the mitral valve annulus for mounting in the mitral annular ring platform. This approach provides a consistent platform for accepting valved-stent mitral valve prosthetic devices from different vendors to be used.

12 Claims, 19 Drawing Sheets
(18 of 19 Drawing Sheet(s) Filed in Color)

Related U.S. Application Data continuation of application No. 14/366,943, filed as application No. PCT/US2012/070785 on Dec. 20, 2012, now Pat. No. 10,321,988.

(60) Provisional application No. 61/578,382, filed on Dec. 21, 2011.

(52) U.S. Cl.
 CPC ............... *A61B 2017/00606* (2013.01); *A61B 2017/00867* (2013.01); *A61F 2/2436* (2013.01); *A61F 2/2445* (2013.01); *A61F 2210/009* (2013.01); *A61F 2220/0025* (2013.01); *A61F 2230/0095* (2013.01); *A61F 2250/006* (2013.01)

(56) References Cited

U.S. PATENT DOCUMENTS

| | | |
|---|---|---|
| 6,171,338 B1 | 1/2001 | Talja et al. |
| 6,375,671 B1 | 4/2002 | Kobayashi et al. |
| 6,419,696 B1 | 7/2002 | Ortiz et al. |
| 6,790,229 B1 | 9/2004 | Berreklouw |
| 7,097,659 B2 | 8/2006 | Woolfson et al. |
| 7,125,421 B2 | 10/2006 | Tremulis et al. |
| 7,942,927 B2 | 5/2011 | Kaye et al. |
| 7,951,195 B2 | 5/2011 | Antonsson et al. |
| 8,070,800 B2 | 12/2011 | Lock et al. |
| 2002/0010481 A1 | 1/2002 | Jayaraman |
| 2005/0149178 A1 | 7/2005 | Spence |
| 2005/0222488 A1 | 10/2005 | Chang et al. |
| 2005/0222489 A1 | 10/2005 | Rahdert et al. |
| 2005/0228495 A1 | 10/2005 | Macoviak |
| 2006/0052821 A1 | 3/2006 | Abbott et al. |
| 2006/0058871 A1 | 3/2006 | Zakay et al. |
| 2006/0106279 A1 | 5/2006 | Machold et al. |
| 2007/0016288 A1 | 1/2007 | Gurskis et al. |
| 2007/0038296 A1 | 2/2007 | Navia et al. |
| 2007/0185571 A1 | 8/2007 | Kapadia et al. |
| 2007/0293944 A1 | 12/2007 | Spenser et al. |
| 2008/0077235 A1 | 3/2008 | Kirson |
| 2008/0243245 A1 | 10/2008 | Thambar et al. |
| 2009/0005863 A1 | 1/2009 | Goetz et al. |
| 2009/0157174 A1 | 6/2009 | Yoganathan et al. |
| 2009/0192585 A1* | 7/2009 | Bloom ...................... A61F 2/82 |
| | | 623/1.26 |
| 2009/0281557 A1 | 11/2009 | Sander et al. |
| 2009/0326648 A1 | 12/2009 | Machold et al. |
| 2010/0076549 A1 | 3/2010 | Keidar et al. |
| 2010/0145440 A1 | 6/2010 | Keraenen |
| 2010/0262232 A1 | 10/2010 | Annest |
| 2010/0292785 A1 | 11/2010 | Seguin et al. |
| 2010/0312333 A1 | 12/2010 | Navia et al. |
| 2010/0318183 A1 | 12/2010 | Olli |
| 2010/0331971 A1 | 12/2010 | Keraenen et al. |
| 2011/0152886 A1 | 6/2011 | Sato et al. |
| 2011/0245911 A1 | 10/2011 | Quill et al. |
| 2011/0295055 A1 | 12/2011 | Albrecht et al. |
| 2012/0016464 A1 | 1/2012 | Seguin |
| 2013/0006352 A1 | 1/2013 | Yaron |

FOREIGN PATENT DOCUMENTS

| | | |
|---|---|---|
| WO | 02/41789 A2 | 5/2002 |
| WO | 2003/020179 A1 | 3/2003 |
| WO | 2005062980 A2 | 7/2005 |
| WO | 2006/111391 A1 | 10/2006 |
| WO | 2007/081820 A1 | 7/2007 |
| WO | 2012/103204 A2 | 8/2012 |
| WO | 2013/096541 A1 | 6/2013 |

OTHER PUBLICATIONS

International Application No. PCT/US12/70785: International Search Report And Written Opinion dated Mar. 13, 2013, 13 pages.
Extended European Search Report mailed in EP 25203694.2 on Feb. 12, 2026 (5 pages).

* cited by examiner

A  B  C

Medtronic Melody®
Transcatheter
Pulmonary Valve

Medtronic-CoreValve
Revalving

Edwards Sapien
Transcatheter Heart
Valve

PLATFORMS FOR MITRAL AND/OR TRICUSPID VALVE REPLACEMENT

CROSS-REFERENCE TO RELATED APPLICATIONS

The present application is a continuation of U.S. Ser. No. 16/117,103, filed Aug. 30, 2018, which is a continuation of U.S. Ser. No. 14/366,943, filed Jun. 19, 2014, which is the National Stage of International Application No. PCT/US2012/070785, filed Dec. 20, 2012, which claims the benefit of priority to U.S. Provisional Patent Application No. 61/578,382, filed Dec. 21, 2011, the entire contents of each of which are incorporated herein by reference.

TECHNICAL FIELD

The present invention relates to mitral valve prosthetic devices and, more particularly, to platforms into which mitral valve prosthetic devices may be deployed percutaneously and/or transapically.

BACKGROUND

The use of a catheter based percutaneous valved stent has been shown to be feasible in replacing both the human pulmonic and aortic valves. The pulmonic valve was the first to be successfully replaced by a percutaneous approach and is the furthest along in development (FIG. 1A). There are currently two aortic valve products in clinical trials (FIG. 1B and FIG. 1C) and more in development that are deployed percutaneously. While there is a great deal of interest in replacing the mitral valve percutaneously, the anatomy and function of the mitral valve prevents direct application of the current aortic/pulmonic technology.

In addition to the percutaneous catheter-based aortic valve replacement devices illustrated in FIG. 1, there are three other types of replacement valve prosthesis known to the applicants that use different technologies. One known technology, named the Transcatheter Mitral Valve Implantation (TMVI), is being developed by CardiAQ Valve Technologies (CVT). This design is more of a basic stent which lacks a sufficient anchoring mechanism. The TMVI is in a very preliminary design phase and, to date, has not been tested repeatedly with success in animal models. A second known technology is being developed by EndoValve. The Endo-Valve design is not stent based but relies on a tripod anchoring system with a central supporting strut. A device to be used with this technology will be introduced by minimally invasive surgical techniques. A third known minimally invasive off pump mitral valve replacement device is being developed by Georg Lutter's group at the University of Kiel in Germany. Their design is stent based but requires placement through the apex of the left ventricle (LV). Surgically manipulating the LV apex through a small incision can be relatively dangerous particularly in patients with CHF and IMR. This is a relative negative for that design as it is more desirable to access the mitral valve via the safer and more forgiving lower pressure left atrium. The anchoring mechanism is also awkward in that it relies on a chord from the implant being brought out through the LV apical incision and secured in the closure of that incision. This anchoring strategy also precludes the device ever evolving to the point of being placed via a peripheral blood vessel.

There are also a large group of percutaneous mitral valve repair devices that have been developed to date. The majority of these devices have tried to exploit the proximity of the coronary sinus to the mitral valve annulus to perform some type of "annuloplasty" to limit mitral regurgitation. The basic premise behind all of them is to place a device in the coronary sinus that will shrink the valve orifice and thus decrease mitral regurgitation. However, none of these techniques has shown reproducible efficacy in human trials despite almost 10 years of development work. The most successful percutaneous mitral valve repair technique is EValve's MitraClip® System. This device is used to clip the mitral leaflets together to limit mitral regurgitation. Unfortunately, the clip system has significant down sides. It can be very difficult and tedious to master technically and even in expert hands can take hours to place. Also, it does not eliminate MR; it only limits it. It does not approximate the success of surgical mitral valve repair or replacement and as such is only a temporizing strategy.

The mitral valve replacement platforms described herein are designed to assist patients who suffer from ischemic mitral valve regurgitation (IMR). The majority of patients with IMR would benefit from valve replacement but are too sick to withstand the morbidity of standard valve replacement procedures. This population of patients in the United States alone is estimated to be 1.2 to 2.1 million patients, with approximately 425,000 patients having moderate or severe IMR with heart failure. IMR results from left ventricular (LV) distortions caused by a myocardial infarction (MI) or heart attack. Patients with this disease survive their heart attack but the resulting injury causes the ventricle to dilate and fail over months and years. In many cases this congestive heart failure (CHF) is worsened by IMR. Patients with CHF and IMR can become extremely sick and be very hard to manage medically. Most clinicians agree that a competent mitral valve would make the management of these patients much more straight-forward and cost effective.

Accordingly, there is a significant need for percutaneous mitral valve replacement technologies that are appropriately configured to account for the dimensions and geometry of the mitral valve. It would be advantageous to have a device that can be deployed percutaneously and/or transapically to create a platform at the mitral valve position that reduces the diameter to an appropriate and uniform size/dimension for subsequent percutaneous and/or transapical implantation of a valved-stent. The invention provides several embodiments of such a device.

SUMMARY

The present inventors have addressed the above needs in the art by providing a mitral valve prosthesis that is percutaneously and/or transapically deployed in at least two stages. In a first stage, a mitral annular platform adapted for percutaneous and/or transapical delivery is delivered to and anchored in the mitral valve annulus. In the second stage, a valved-stent mitral valve prosthetic device adapted for percutaneously and/or transapical delivery is delivered to the mitral valve annulus for mounting in the mitral annular ring platform. This approach provides a consistent platform for accepting valved-stent mitral valve prosthetic devices from different vendors to be used.

Several embodiments of the mitral annular platform are provided in accordance with the invention.

In a first embodiment, the mitral annular platform includes a plurality of wires preformed into separate but contiguous helices. At least one of the helices is adapted to serve as an anchor on the atrial side of the mitral annulus, and at least one of the helices is adapted to serve as an anchor on the ventricular side of the mitral annulus. At least one of the helices traverses the mitral annulus, connecting the atrial and mitral helices to each other. In total, the helices combine to serve as a landing zone for subsequent percutaneous valved-stent implantation.

In a second embodiment, the mitral annular platform is anchored to the atrial septum. Left and right discs straddle the atrial septum and have a central hollow region therebetween so as to allow left atrial access from the right atrium when the discs are deployed in a heart. The mitral annular ring platform includes at least one disc adapted to fit into the mitral valve annulus. A mitral annular ring adapted to be implanted in an atrial septum is deployed across a mitral valve orifice and to accept the valved-stent mitral valve prosthesis. Once a valved-stent device is implanted into the mitral annular ring, a plug is deployed to close the hollow central region between the left and right atrial discs.

In a third embodiment, the mitral annular platform includes a first magnetic ring having a first polarity and adapted for placement in a left atrium in a supra mitral annular position via a patient's femoral (jugular, or subclavian) vein, and a second magnetic ring having a second polarity and adapted for placement on a ventricular side of the mitral annulus via a femoral artery and/or transapically (from the LV apex). The first and second magnetic rings are brought together to lock together magnetically so as to sandwich mitral valve tissue and mitral annulus circumferentially when deployed.

In a fourth embodiment, the mitral annular platform includes a first petal-shaped wire ring having a hollow center and adapted for placement on an atrial side of the mitral annulus so as to exert downward pressure, and a second petal-shaped wire ring having a hollow center and adapted for placement on a ventricular side of the metal annulus so as to exert upward pressure. When deployed, the first and second petal-shaped wire rings overlap in central region thereof to apply opposing pressures.

These and other like embodiments are within the scope of the invention as described in the following detailed description and claimed in the attached claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The various novel aspects of the invention will be apparent from the following detailed description of the invention taken in conjunction with the accompanying drawings, of which.

DETAILED DESCRIPTION OF ILLUSTRATIVE EMBODIMENTS

The invention will be described in detail below with reference to FIGS. 1-18. Those skilled in the art will appreciate that the description given herein with respect to those figures is for exemplary purposes only and is not intended in any way to limit the scope of the invention. All questions regarding the scope of the invention may be resolved by referring to the appended claims.

Overview

The mitral valve annulus is non-uniform, non-planar, dynamic structure. Percutaneously anchoring a replacement valve securely in this location in the absence of a surgically placed annuloplasty ring remains a significant challenge. The embodiments described below were designed to permit the percutaneous and/or transapical stepwise construction of a platform or "landing zone" in the mitral space to facilitate subsequent implantation of a percutaneously placed replacement valve. The designs vary but are linked by the overarching concept of a percutaneous and/or transapical platform construction to facilitate percutaneous mitral valve device anchoring and perivalvular seal. The advantage to these approaches to "landing zone" construction is that each can be performed percutaneously and/or transapically without need for a large incision or cardiopulmonary bypass.

A successful percutaneously and/or transapically placed mitral valve requires four major design characteristics:
1. Foldability
2. Anchoring mechanism
3. Perivalvular sealing mechanism
4. Functioning valve mechanism Several embodiments are described herein of platforms that meet these design characteristics and that may be deployed percutaneously and/or transapically for accepting a percutaneously and/or transapically deployed mitral valve prosthetic. In each embodiment, a mitral valve is replaced using percutaneous and/or transapical techniques in a multiple stage operation. In a first stage, a mitral annular platform is inserted as an anchoring or mooring spot ("landing zone") for a valved-stent mitral valve prosthetic device. Then the valved-stent mitral valve prosthetic device is mounted to the platform in a separate transcutaneous insertion operation. This allows the use of valves from different vendors. Four different embodiments are described, although further related platform embodiments may become apparent to those skilled in the art based on the following descriptions.

First Embodiment—Helical Platform

Figure 2:
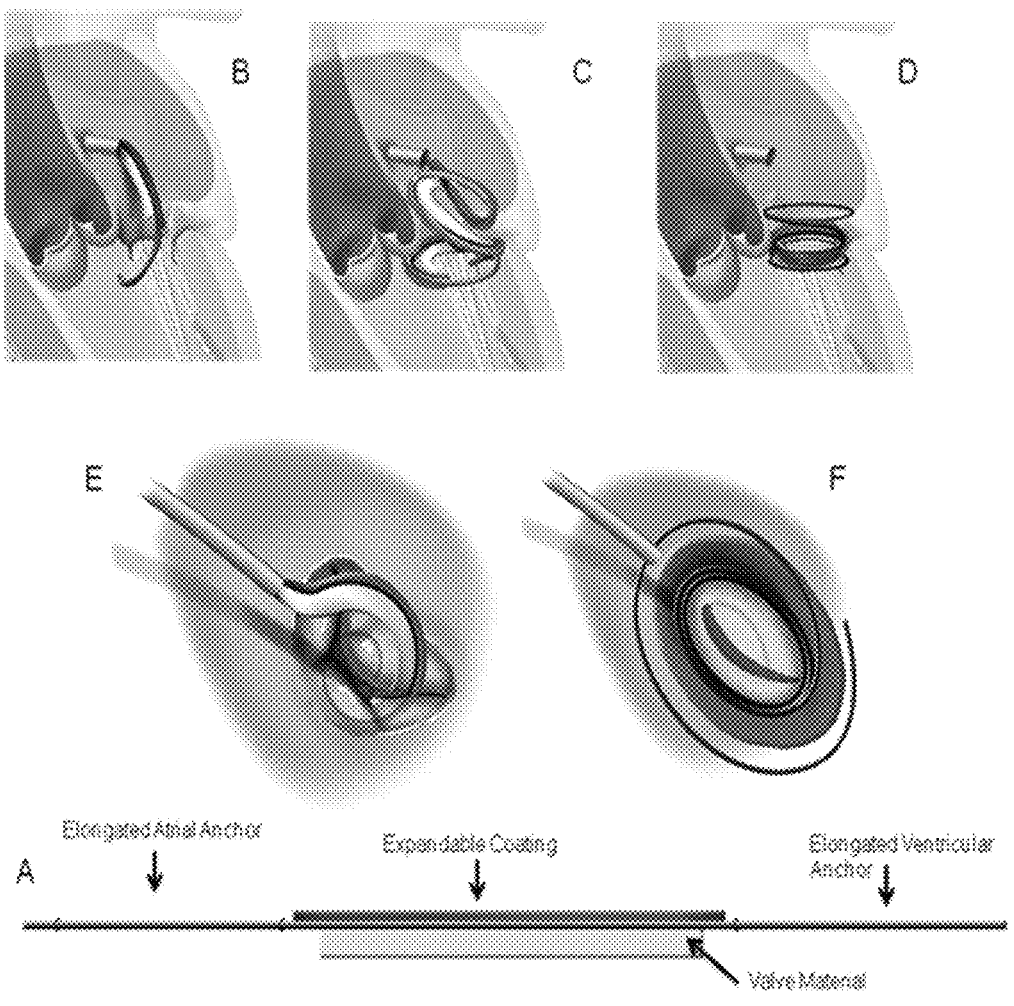
FIG. 2 illustrates a mitral valve replacement platform in accordance with a first embodiment of the invention where helices are extended for percutaneous delivery and then wound in the valve position to form an anchoring mechanism and a sealing cuff.

In this embodiment, a single, thick nitinol wire is preformed into three separate but contiguous helices that are inserted percutaneously and/or transapically to provide a "landing zone" or anchoring mechanism to facilitate the placement of simple valved stents in the mitral position. As shown in FIG. 2, the leading helix has 1 to 2 coils and is large enough in diameter to serve as the left ventricular anchor for the valve. The second helix is comprised of at least one but potentially as many as 5 to 6 more tightly wound coils of a smaller diameter that are designed to fit snuggly in the annulus. This part of the coil may be coated with a bi-layer material composed of a super absorbent substance that expands when the valve is in place to prevent perivalvular leakage. The outer layer of the bi-layer is a hydrophobic material that prevents the super absorbent material from expanding while the valve is being placed. This second layer is designed to elute off slowly to ultimately allow the underlying superabsorbent material to expand once the valve is positioned appropriately. The inter-annular portion of the coil also may be fitted with a bioprosthetic valve leaflet material that folds into a functional valve mechanism when the device assumes its coiled position. The last helix is similar to the first and serves as the atrial anchoring mechanism. When locked into position, the mitral annulus is "sandwiched" between the leading and trailing helices, with the valve leaflets centrally positioned in the annulus.

Figure 1:
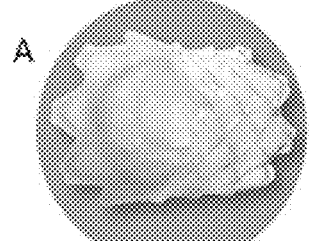
FIG. 1 illustrates prior art pulmonic valve (FIG. 1A) and aortic valve (FIGS. 1B and 1C) prosthetics.
Figure 1:
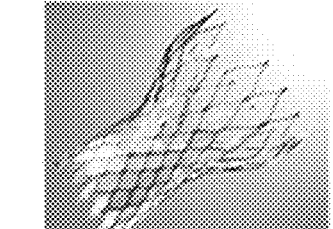
Figure 1:
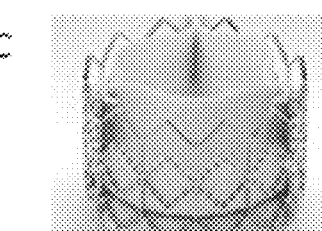
Figure 3:
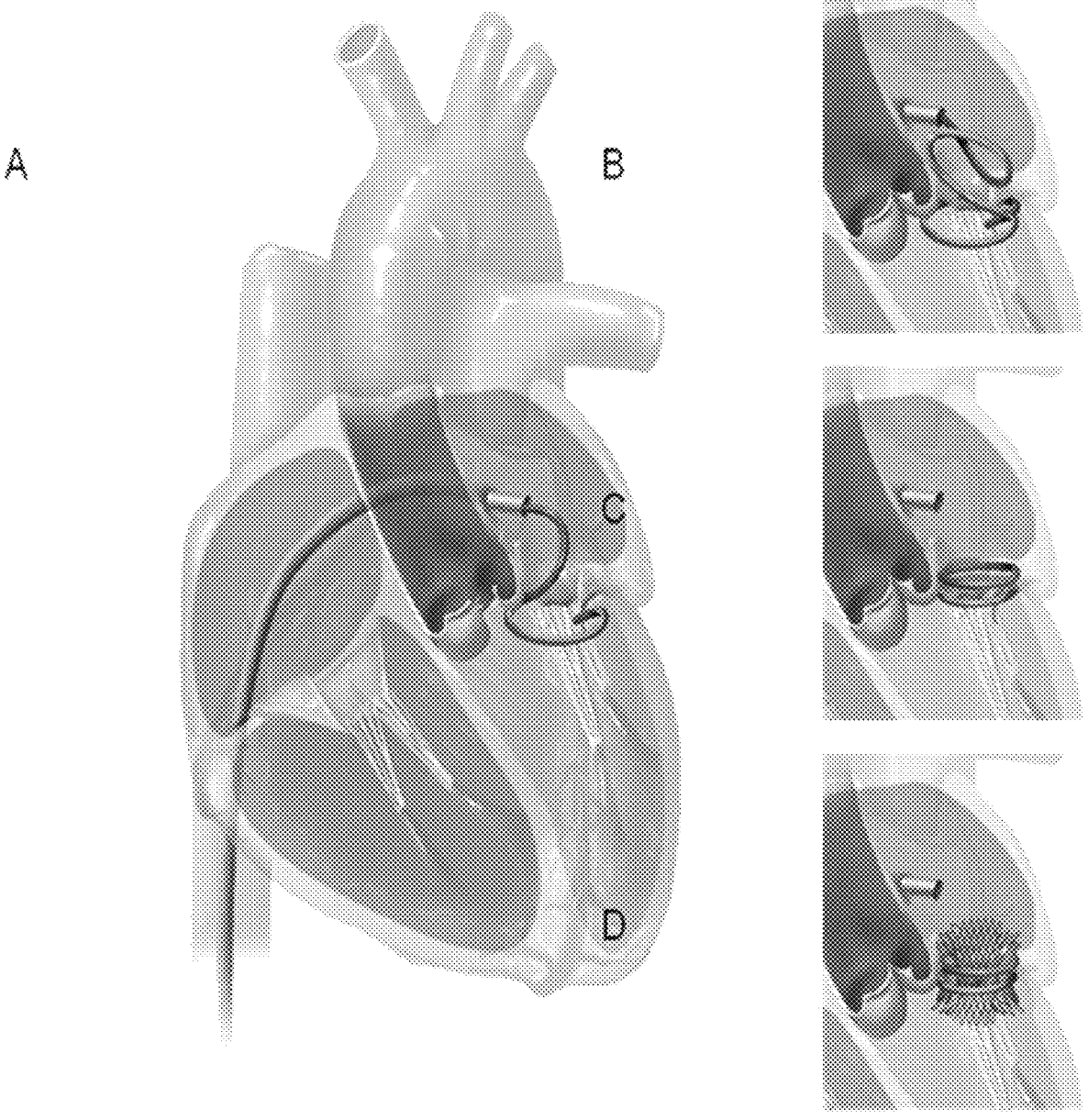
FIG. 3 illustrates the helical anchoring embodiment of FIG. 2 for facilitating mitral valve replacement using a simple valved stent anchored by percutaneously deployed helical coils.
Figure 4:
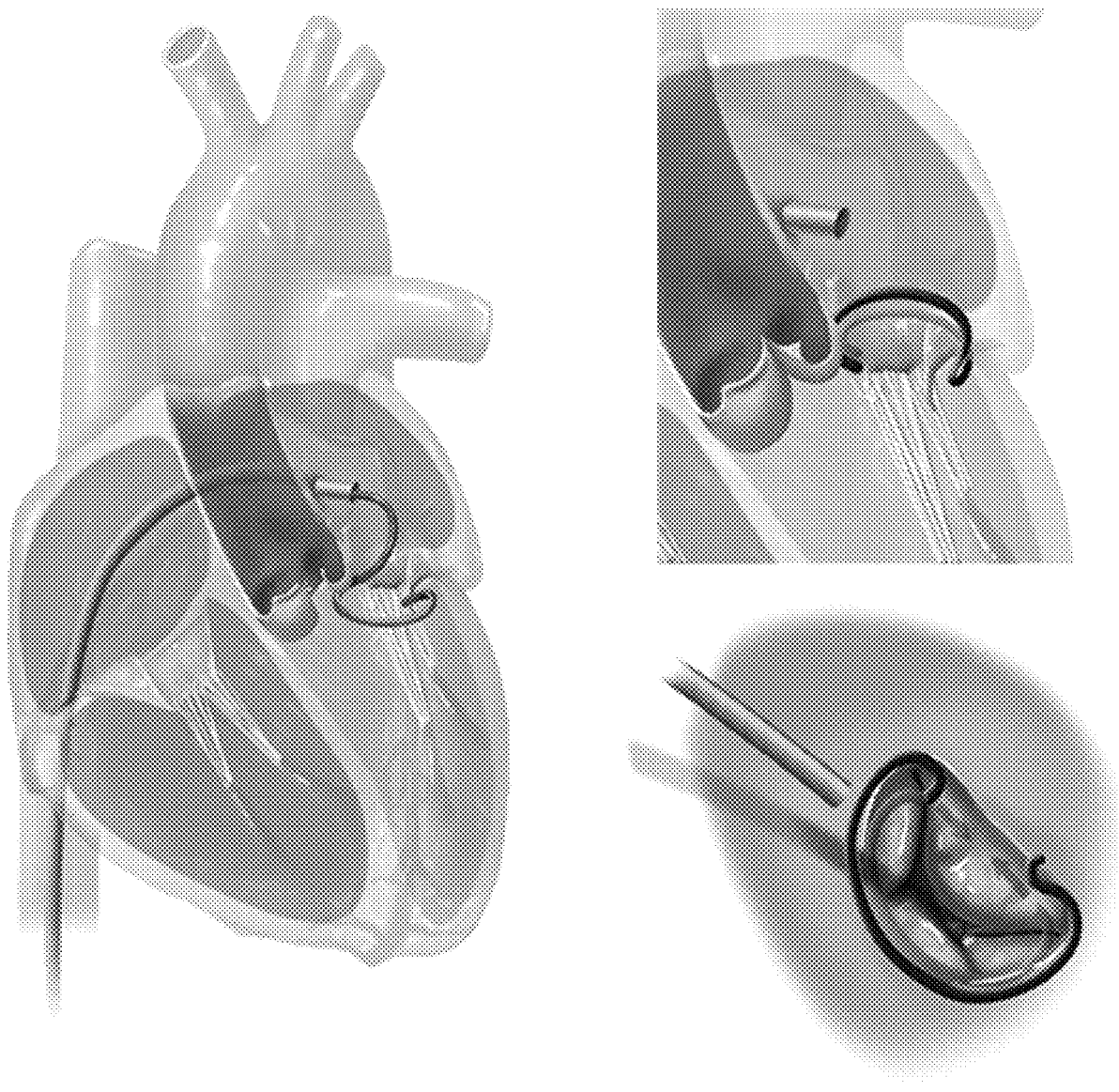
FIG. 4 illustrates the helical anchoring embodiment of FIG. 2 for providing percutaneous reduction annuloplasty.

The helical coil design of this embodiment also may be adapted to provide a "landing zone" or anchoring mechanism to facilitate the placement of simple valved stents (like the ones currently being placed clinically in the aortic and pulmonary position, as shown in FIG. 1) in the mitral position as shown in FIG. 3. Thus, the landing zone is deployed as illustrated in FIG. 2 and a valved stent is placed in the landing zone as shown in FIG. 3. Of course, in this embodiment, the inter-annular portion of the coil is not fitted with valve leaflet material. This embodiment also can be adapted to create a catheter based reduction annuloplasty device to decrease annular area and reduce mitral regurgitation as shown in FIG. 4.

Since the helices may be straightened for percutaneous and/or transapical delivery, the valved helical design of this embodiment has the potential to decrease catheter delivery size for percutaneous and/or transapical valve replacement to almost unimaginably small diameters. The helical anchoring platform also allows placement of currently available stented valves, designed for placement in the aortic and pulmonary positions, to be placed in the mitral position. An annuloplasty ring formed from the helices also may potentially provide a non-invasive means to limit MR when valve placement is contra-indicated.

Second Embodiment—Atrial Septal Anchored Mitral Platform (ASAMP)

In this embodiment, a nitinol based device is anchored to the atrial septum that is preformed into a complex 3D shape (FIG. 5A) including left and right atrial discs (e.g. 0.012 inch nitinol donut) that straddle the atrial septum, a central hollow region between the discs to allow for easy left atrial access from the right atrium, and a mitral annular ring-shaped or oval shaped platform designed to lay across the mitral valve orifice. The mitral annular ring platform includes at least one of the discs adapted to fit into the mitral valve annulus. As shown in FIG. 5B, the nitinol device may be compressed for percutaneous and/or transapical delivery. Once in position, a valve-stented device can be passed from the femoral vein, across the atrial septum, and into the mitral annular ring where the device is anchored to the atrial septum.

Figure 5A:
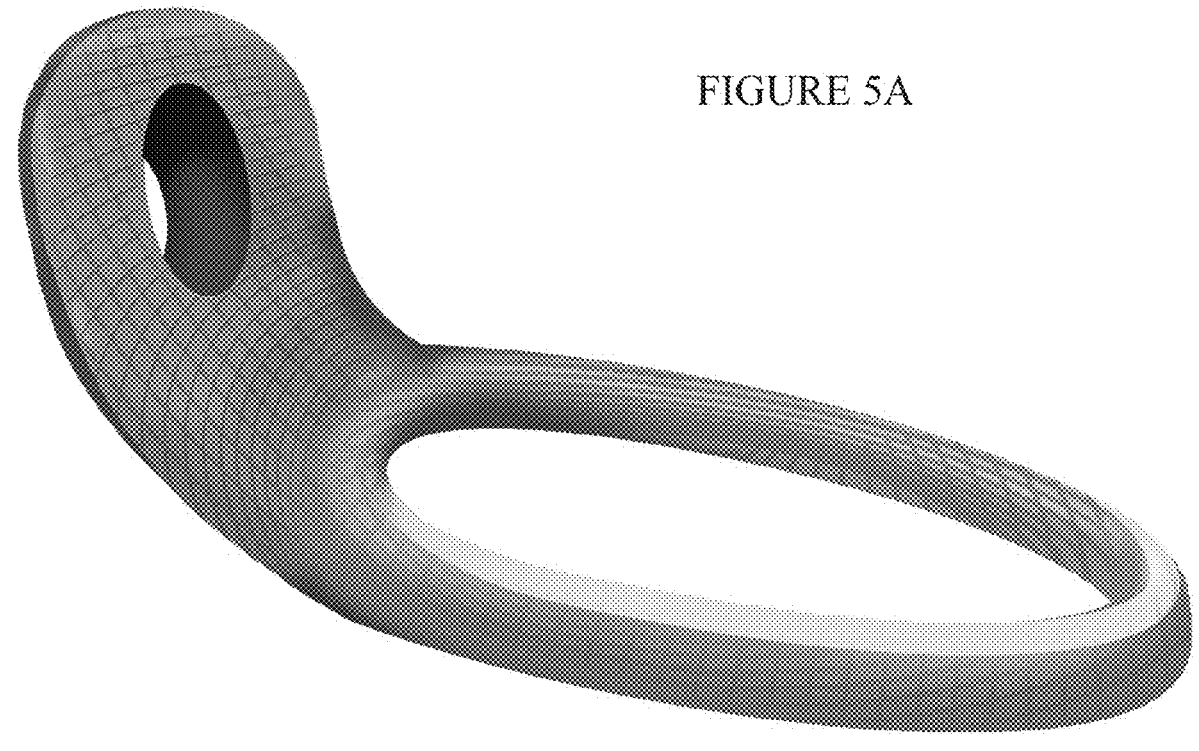
FIGS. 5A and 5B illustrate an atrial septal anchored mitral platform (ASAMP) in accordance with a second embodiment of the invention.
Figure 5B:
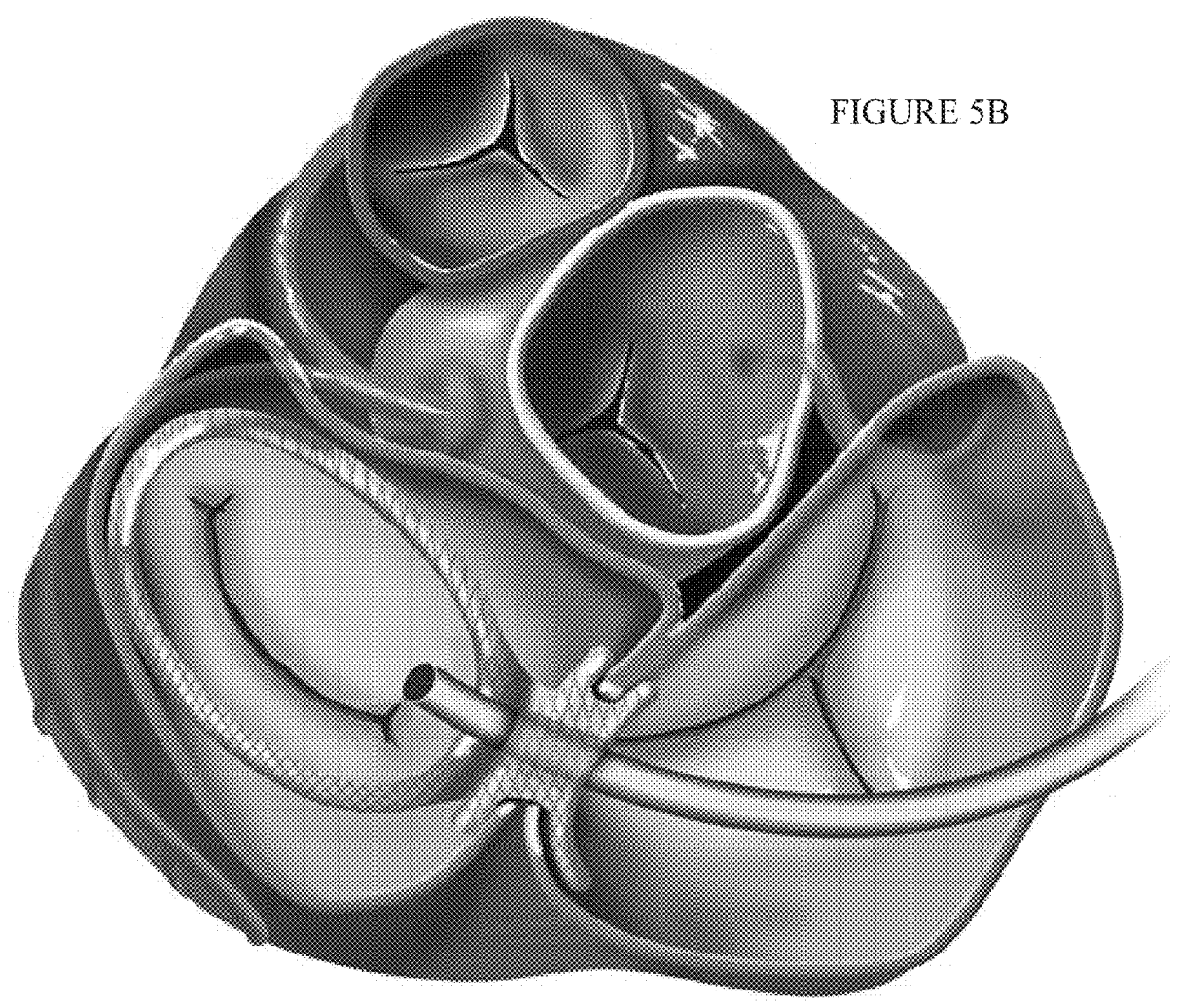
Figure 6:
FIG. 6 illustrates the first step in transeptal delivery of the ASAMP to the left atrium.
Figure 7:
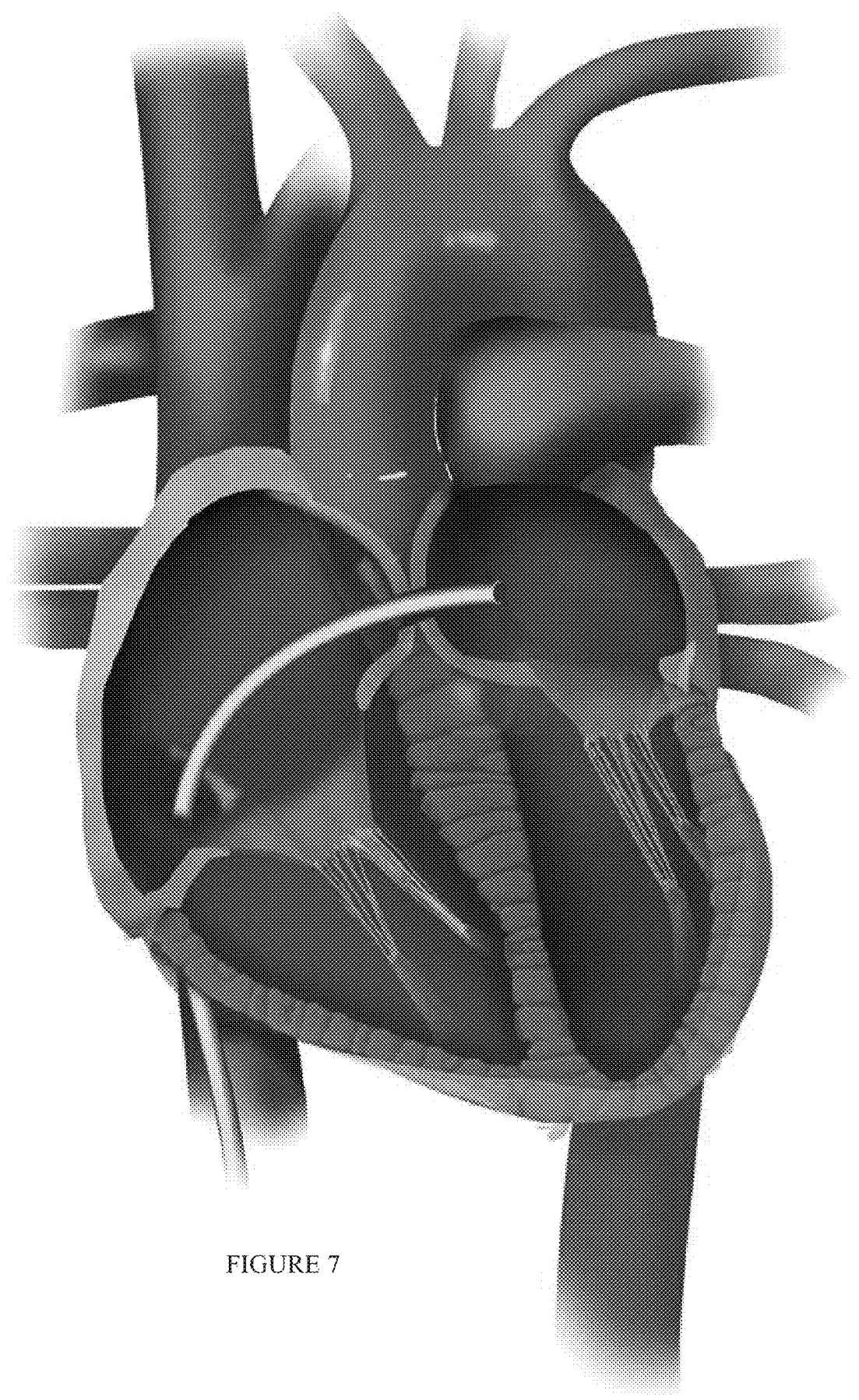
FIG. 7 illustrates the second step in transeptal delivery of the ASAMP to the left atrium.
Figure 8:
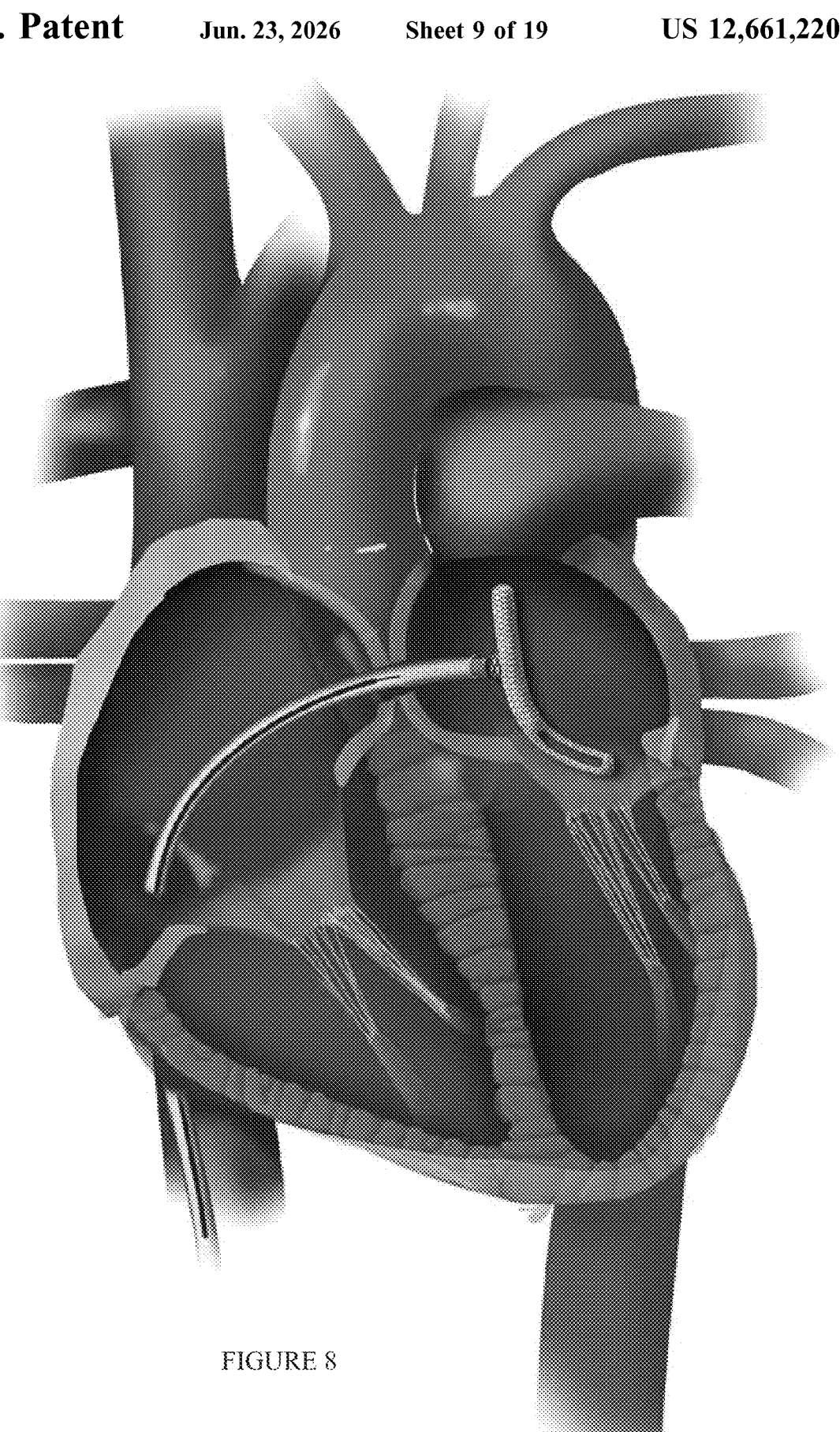
FIG. 8 illustrates partial percutaneous deployment of the ASAMP in the left atrium.
Figure 9:
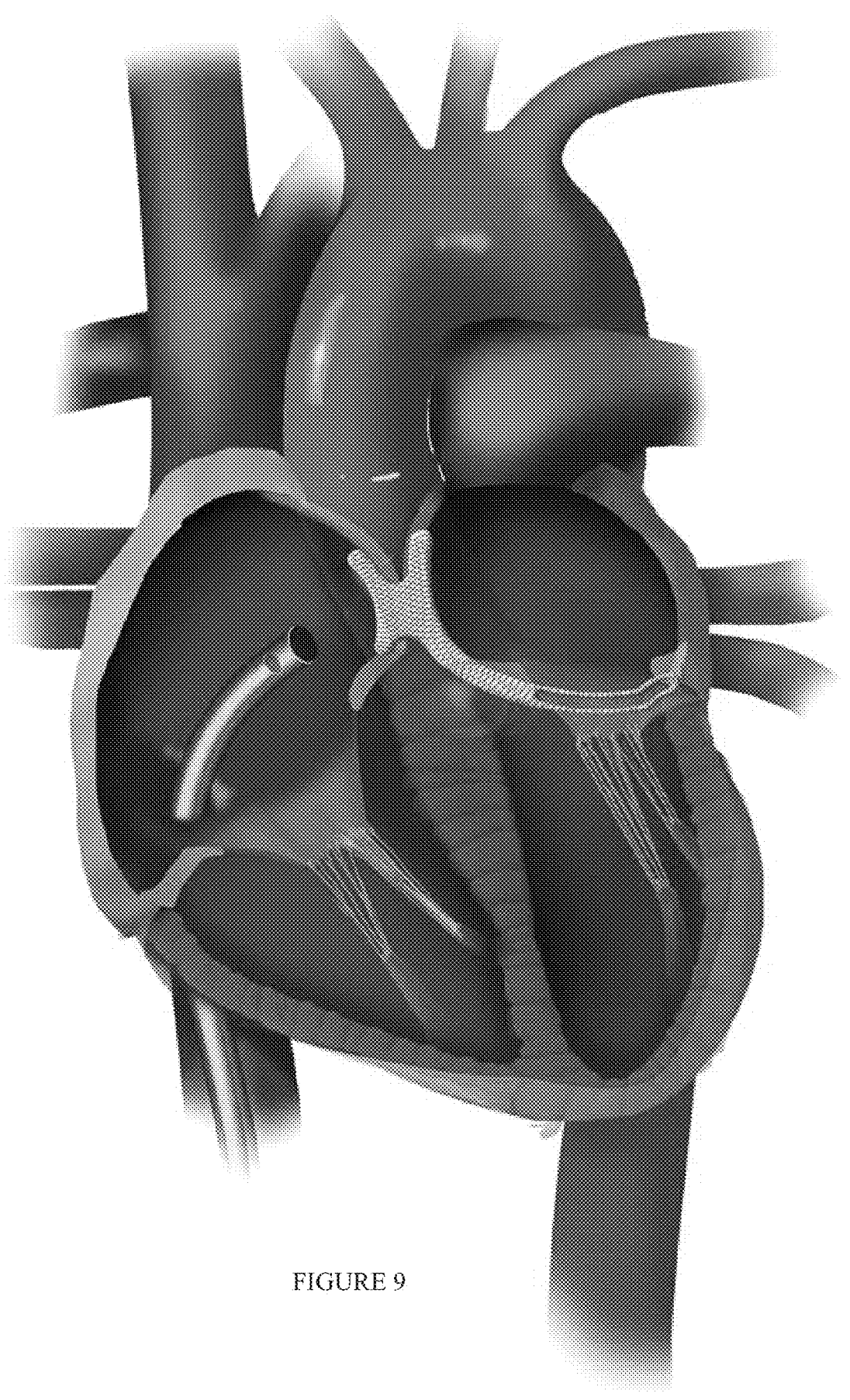
FIG. 9 illustrates the fully deployed ASAMP where the mitral platform is positioned in the mitral valve annulus.
Figure 10:
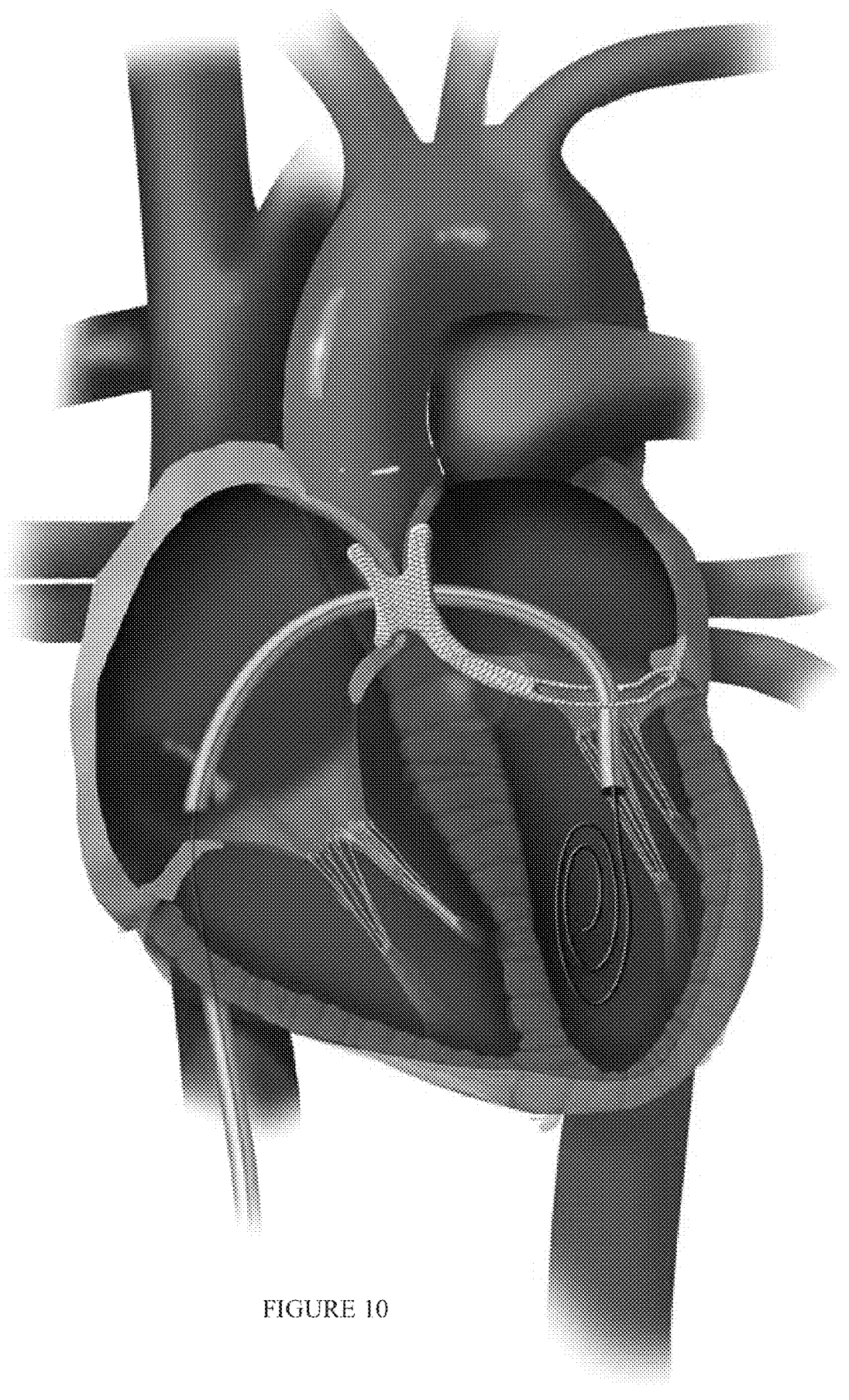
FIG. 10 illustrates the passage of a guide wire into the left ventricle through the mitral annular ring of the ASAMP.
Figure 11:
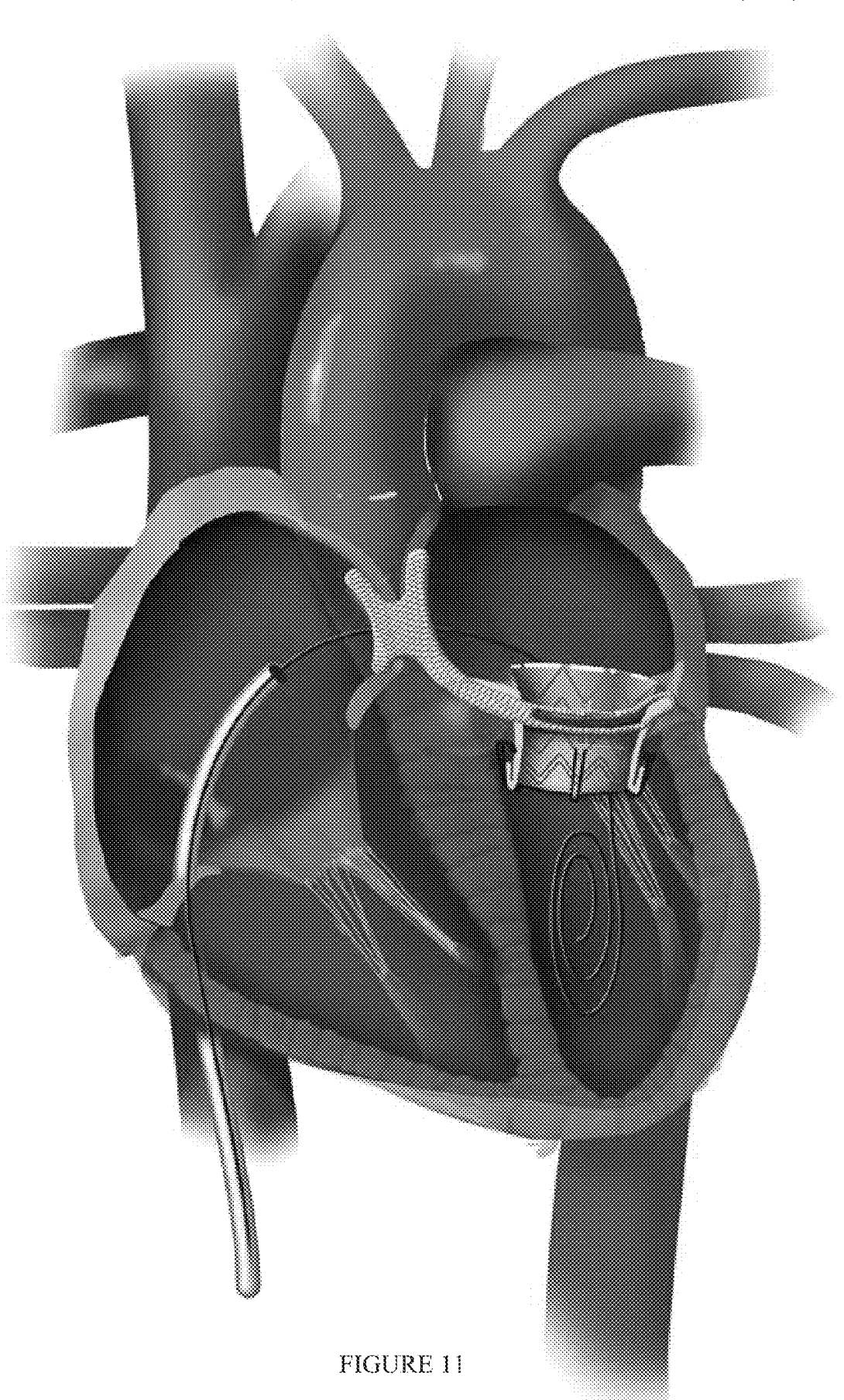
FIG. 11 illustrates deployment of a mitral valve stented prosthetic over a guide wire into the mitral valve annulus for mounting in the ASAMP.
Figure 12:
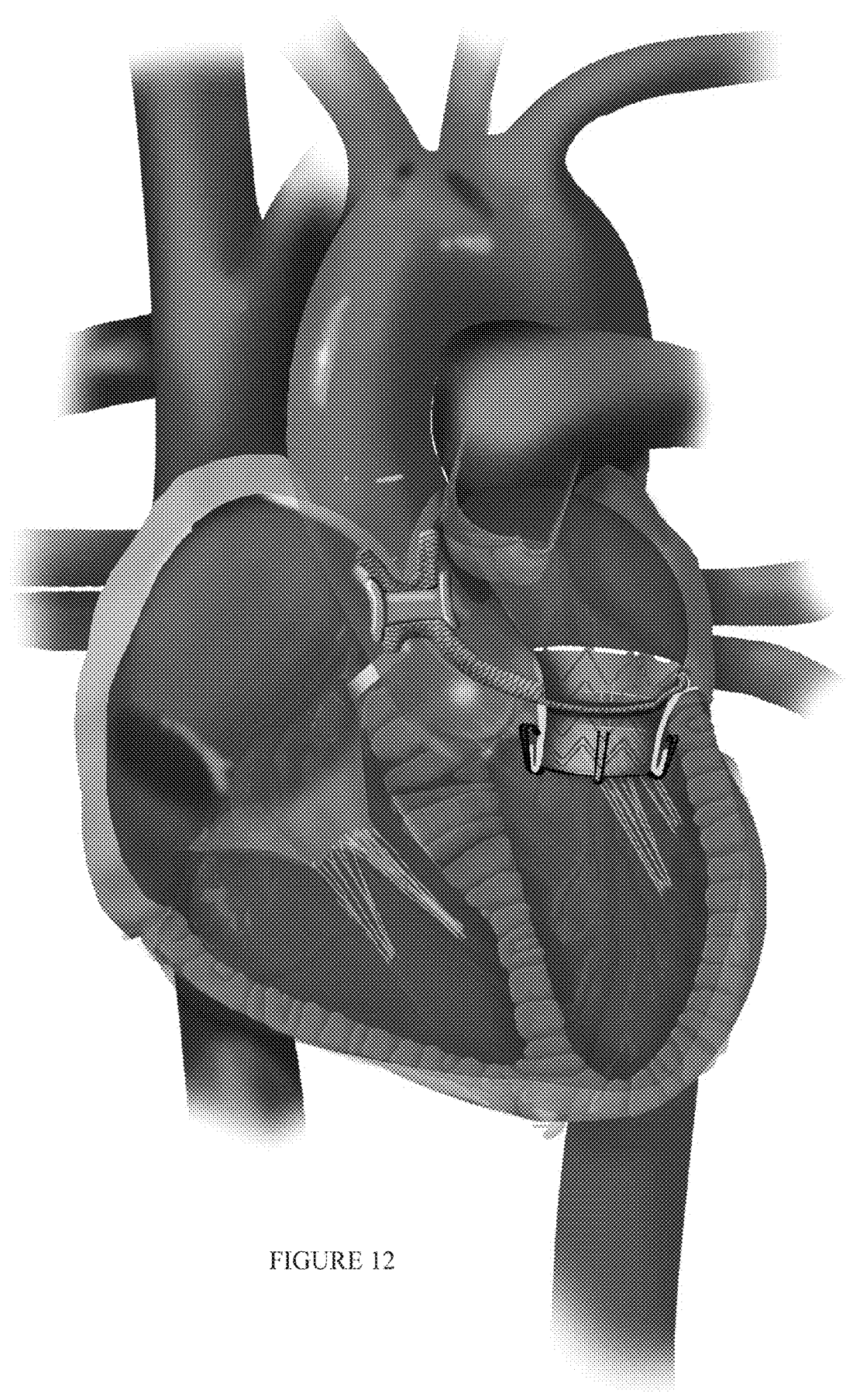
FIG. 12 illustrates the fully deployed ASAMP with the mitral valve stented prosthetic with the hollow portion of the ASAMP device plugged using a custom designed nitinol plug.

The device of FIGS. 5A and 5B is implanted into the atrial septum using standard percutaneous and/or transapical transeptal techniques. In accordance with such techniques, a transeptal delivery catheter is guided into the left atrium as shown in FIG. 6. A delivery sheath (e.g. 12-16 French) is guided into the left atrium as shown in FIG. 7. The compressed device of FIG. 5A is then guided through the delivery catheter for deployment in the left atrium as shown in FIG. 8. Once in position (i.e., the mitral platform is placed in the mitral valve annulus), the device of FIG. 5A is released from its deployment cable as shown in FIG. 9. Once the platform is so positioned, a valved-stent device can be passed over a guide wire from the femoral vein, across the atrial septum, and into the mitral annular ring as shown in FIGS. 10 and 11. Once the valved-stent device is placed in the correct position and seated securely, the hollow portion of the ASAMP device is plugged using a custom designed nitinol plug as shown in FIG. 12.

Figure 13:
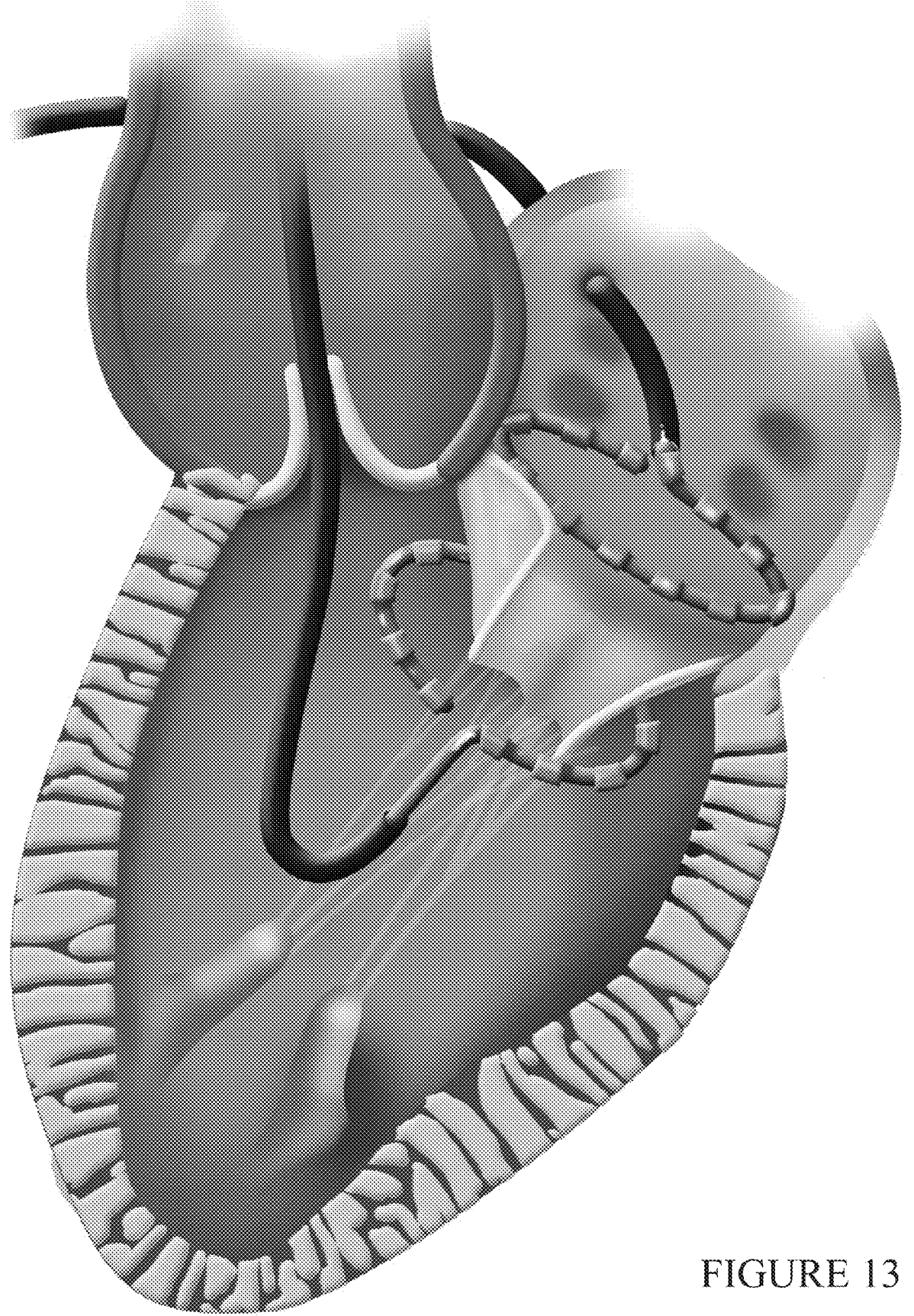
FIG. 13 illustrates the second ring of the third platform embodiment where the second ring is positioned on the ventricular side of the mitral annulus via a retrograde arterial approach.
Figure 14:
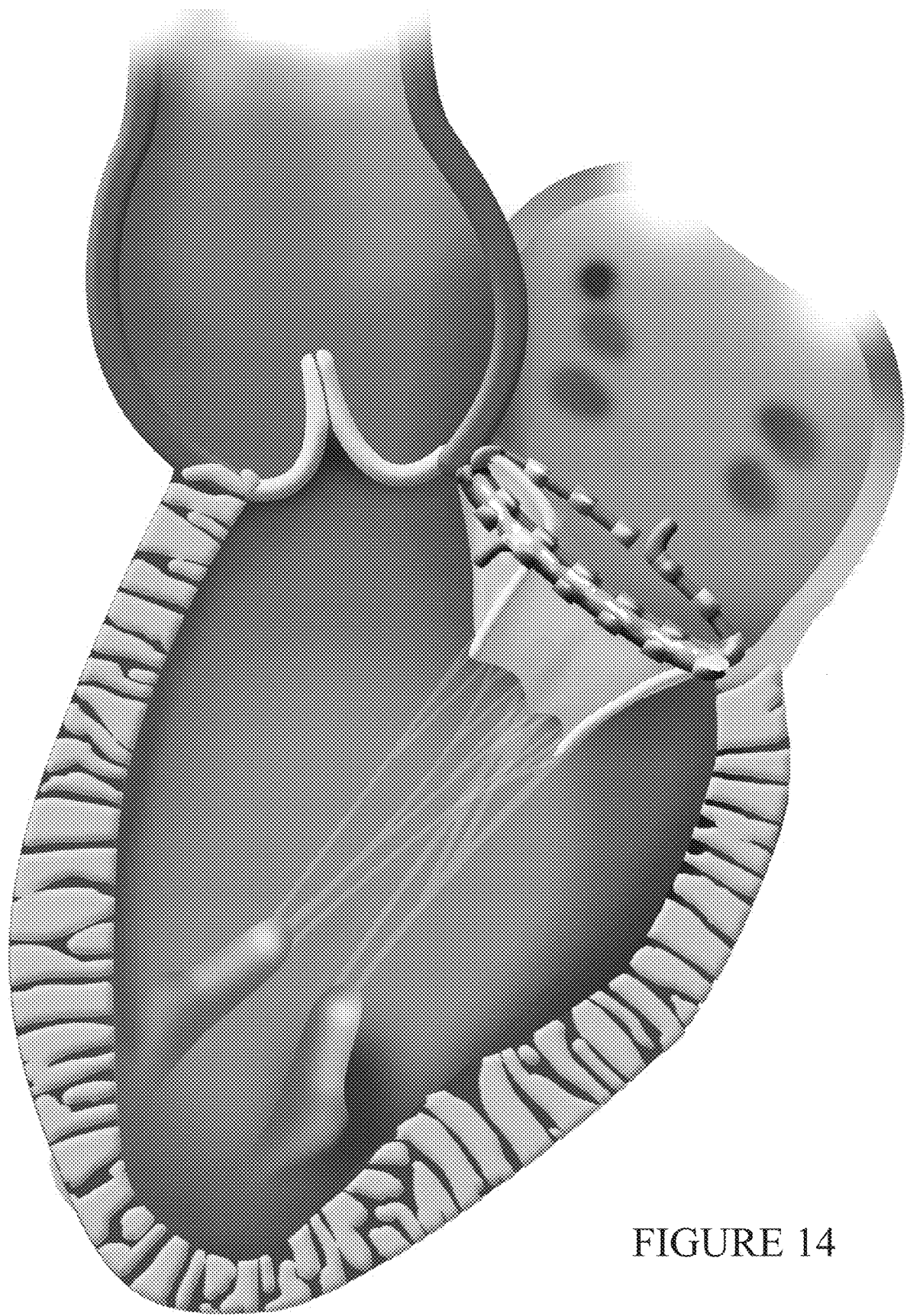
FIG. 14 illustrates a mitral annular ring platform formed from the magnetic rings deployed as illustrated in FIG. 13, where the rings are brought together using their respective delivery catheters and are locked together by the magnetic attraction of the rings so as to sandwich the mitral valve tissue and annulus circumferentially.
Figure 15:
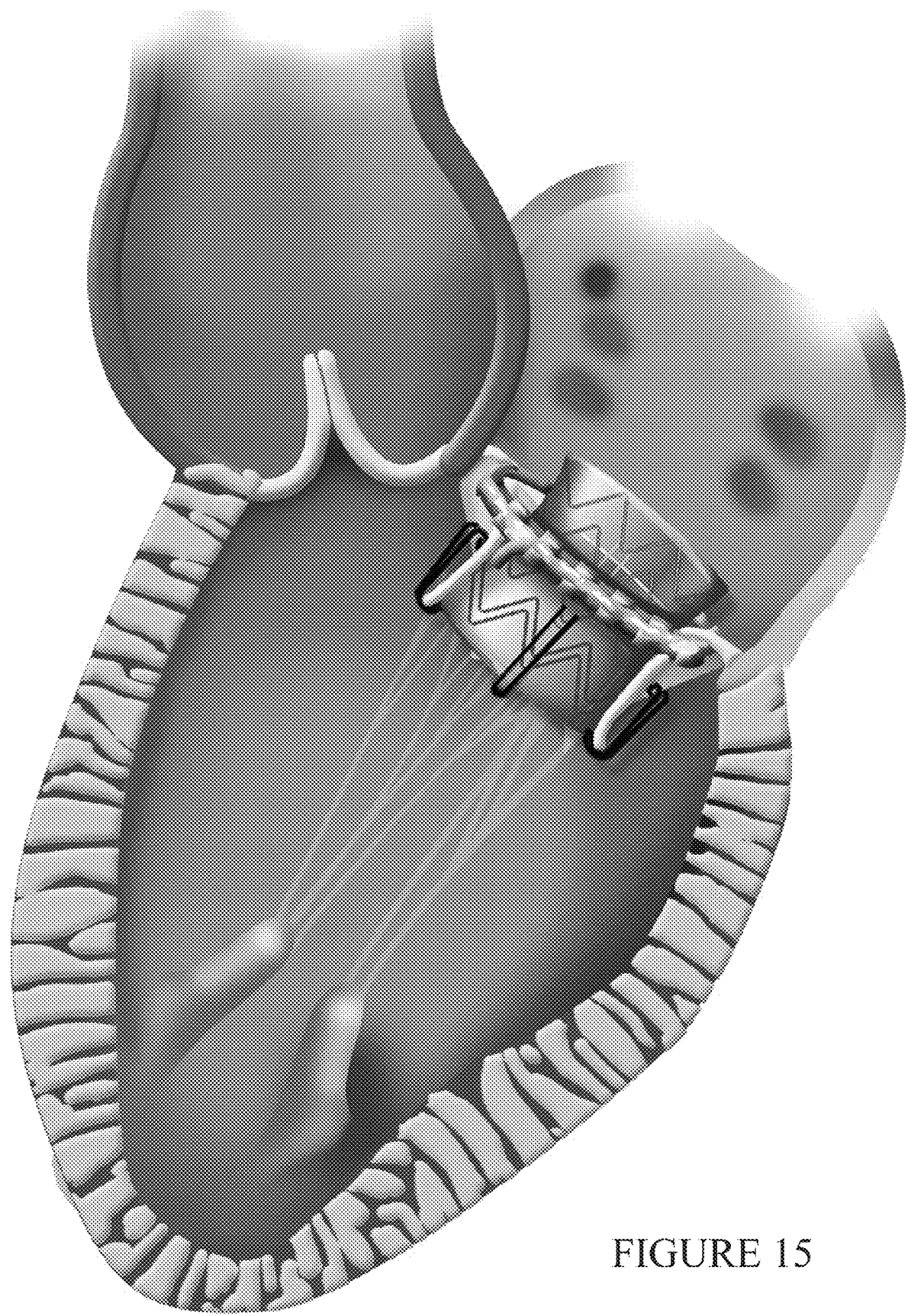
FIG. 15 illustrates a valve-stented device passed from the femoral vein, across the atrial septum, and into the mitral annular ring platform of FIG. 14.
Figure 16:
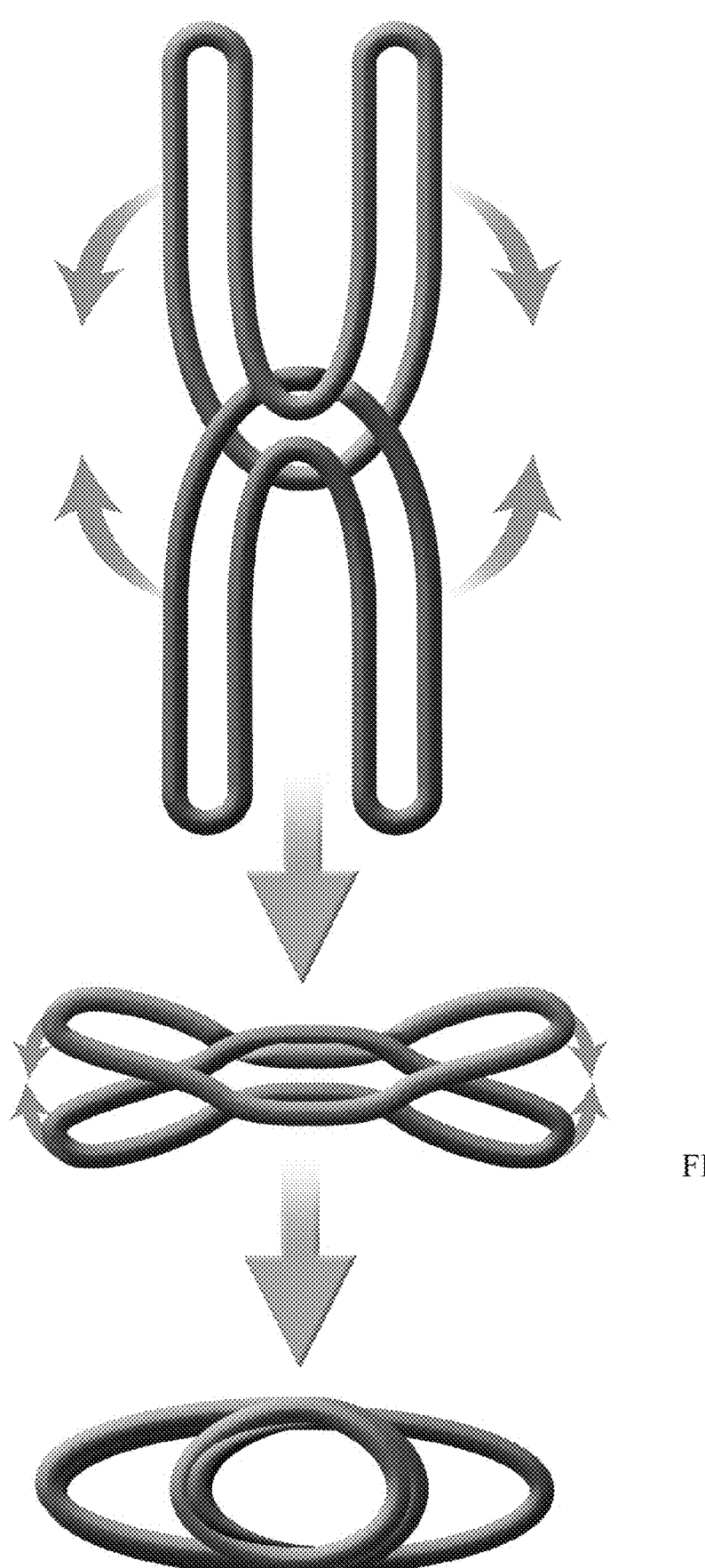
FIG. 16 illustrates a fourth platform embodiment in which two petal-shaped wire rings are joined together and hollow in the center.

Third Embodiment—Percutaneous Annular Mooring (PAM) Using Two Magnetized Rings In this embodiment, two magnetized rings with opposite magnetizations are deployed such that the first ring is positioned in the left atrium in the supra-mitral annular position via the femoral (jugular or subclavian) vein using a standard transeptal approach and the second ring is positioned on the ventricular side of the mitral annulus via a retrograde arterial approach (femoral artery, aorta, aortic valve, left ventricle) as shown in FIG. 13. Once the rings are fully formed in their respective positions, they are brought together using their respective delivery catheters and are locked together by the magnetic attraction of the rings so as to sandwich the mitral valve tissue and annulus circumferentially as shown in FIG. 14. At this point, both rings are released from their delivery catheters. Once in position, a valve-stented device can be passed from the femoral vein, across the atrial septum, and into the mitral annular ring as shown in FIG. 15.

Figure 17:
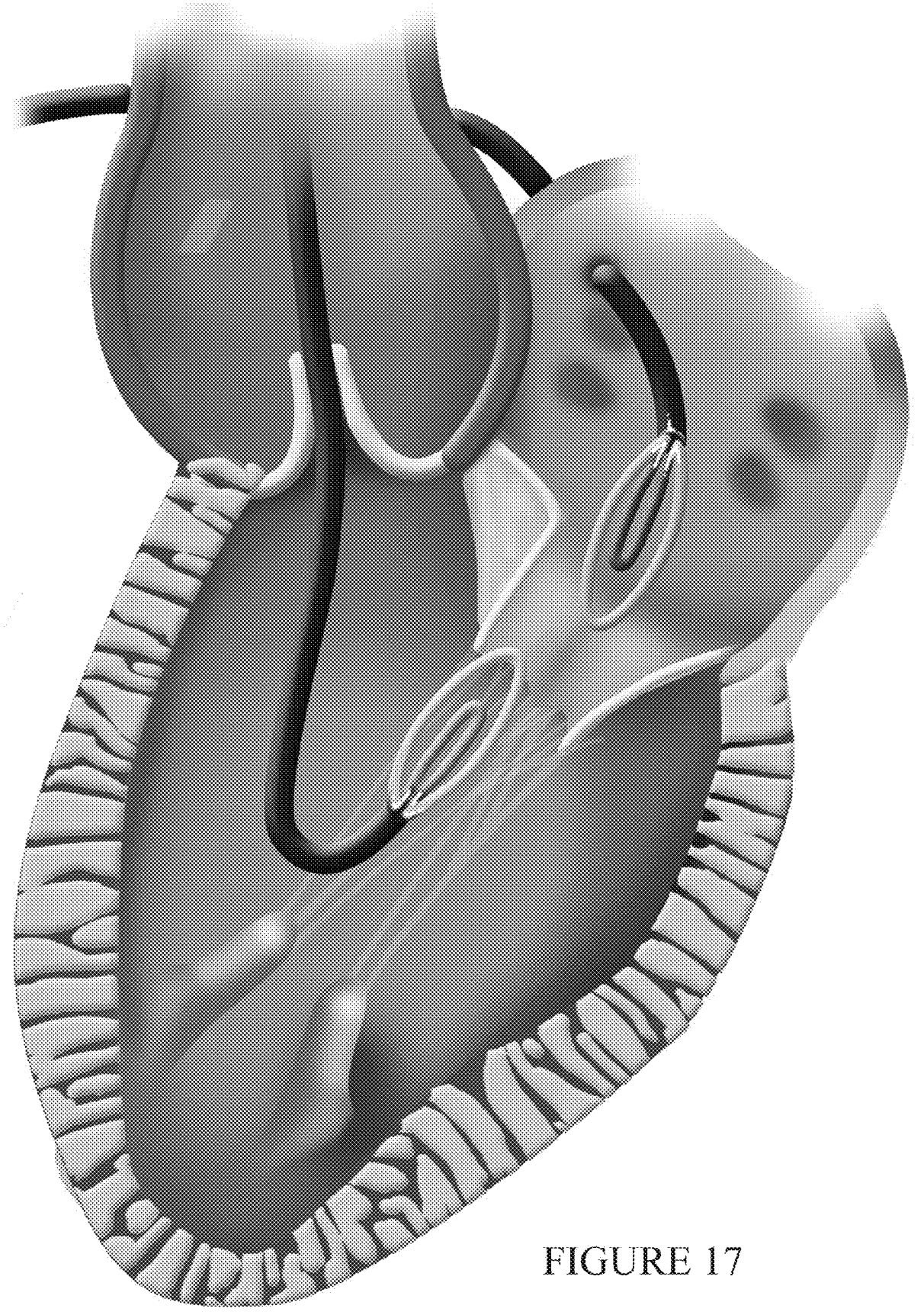
FIG. 17 illustrates that the first ring of the embodiment of FIG. 16 is on the atrial side of the annulus so as to exert a downward pressure and the second ring is on the ventricular side of the annulus so as to exert a counterpressure (upward) to the first ring.
Figure 18:
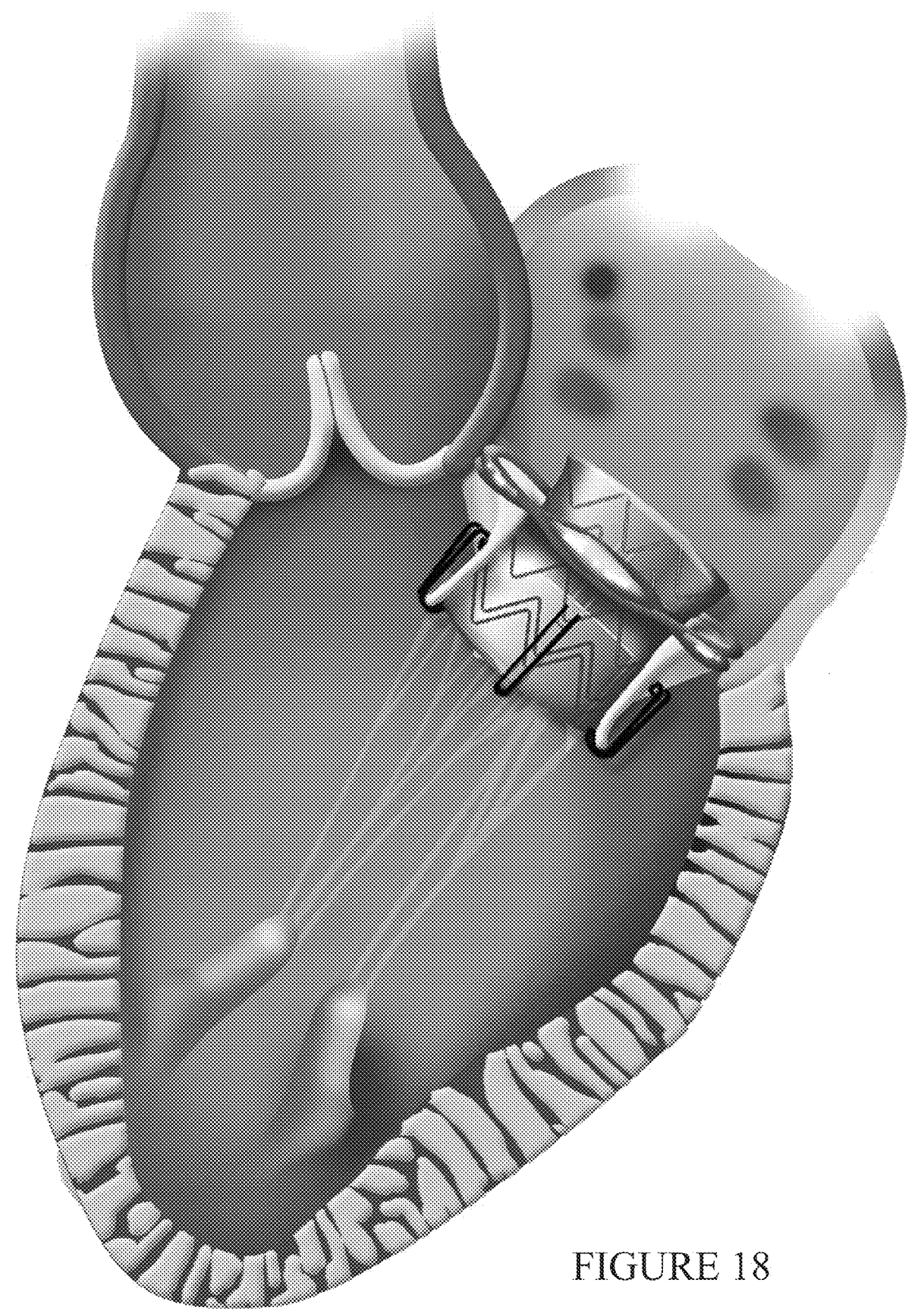
FIG. 18 illustrates a valve-stented device passed from the femoral vein, across the atrial septum, and into the mitral annular ring platform of FIG. 17.

Fourth Embodiment—Percutaneous Annular Mooring (PAM) Using Two Petal-Shaped Wire Rings In this embodiment, two petal-shaped wire rings (FIG. 16) that are joined together and hollow in the center are deployed such that the first ring is on the atrial side of the annulus so as to exert a downward pressure and the second ring is on the ventricular side of the annulus so as to exert a counterpressure (upward) to the first ring as shown in FIG. 17. The rings together sandwich the mitral valve tissue and annulus circumferentially. Once in position, a valve-stented device can be passed from the femoral vein, across the atrial septum, and into the mitral annular ring platform as shown in FIG. 18.

Those skilled in the art will appreciate that the embodiments described herein allow placement of currently available stented valves, designed for placement in the aortic and pulmonary positions, to be placed in the mitral position. The platform devices can be placed through small catheters, making these approaches feasible in children and small adults.

Those skilled in the art will also appreciate that the invention may be applied to other applications and may be modified without departing from the scope of the invention. For example, those skilled in the art will appreciate that the devices and techniques of the invention may be used to replace the tricuspid valve as well as the mitral valve. Also, the devices of the invention may be deployed using venous and/or arterial deployment approaches using techniques known to those skilled in the art. Accordingly, the scope of the invention is not intended to be limited to the exemplary embodiments described above, but only by the appended claims.

What is claimed:

1. An atrioventricular valve prosthesis comprising:

an atrioventricular ring platform structurally configured to be percutaneously and/or transapically delivered to a subject's native atrioventricular valve; and a valved-stent atrioventricular valve prosthetic device, wherein the atrioventricular ring platform comprises wire that when extended from a delivery catheter comprises three preformed, distinct but contiguous sections configured to be inserted when straightened by the delivery catheter to provide an anchoring platform for the valved-stent atrioventricular valve prosthetic device, a first one of the sections comprising at least one leading turn located at a distal end of the wire that is configured to wind the atrioventricular ring platform implant in the subject's native atrioventricular valve and around the subject's native atrioventricular valve leaflets, a second one of the sections comprising at least one intermediate turn and being sized to fit snugly in the annulus of the native atrioventricular valve, and a third one of the sections comprising at least one trailing turn located at a proximal end of the wire, and being configured to maintain a position of the atrioventricular ring platform relative to the subject's native atrioventricular valve prior to the deployment of the valved-stent atrioventricular valve prosthetic device, wherein the atrioventricular ring platform is configured to provide an anchor for the valved-stent atrioventricular valve prosthetic device, and wherein, when the atrioventricular ring platform is locked into position at the native atrioventricular valve, the annulus is sandwiched between the first one and the third one of the sections.

2. The atrioventricular valve prosthesis according to claim 1, wherein the first one of the sections is configured to wind around leaflets and chordae of the subject's native atrioventricular valve.

3. The atrioventricular valve prosthesis according to claim 1, wherein the atrioventricular ring platform is configured to provide a landing zone for the valved-stent atrioventricular valve prosthetic device.

4. The atrioventricular valve prosthesis according to claim 1, wherein the atrioventricular ring platform is configured to create a platform at the subject's native atrioventricular valve that reduces the diameter at a position of the atrioventricular valve in order to provide a suitable size and dimension for subsequent implantation of the valved-stent atrioventricular valve prosthetic device.

5. The atrioventricular valve prosthesis according to claim 1, wherein when the atrioventricular ring platform is configured such that when it is positioned at the subject's native atrioventricular valve, the subject's native atrioventricular valve annulus is between the first and third sections of the platform.

6. The atrioventricular valve prosthesis according to claim 1, wherein the first one of the sections of the atrioventricular ring platform comprises a diameter that is sized relative to the subject's native atrioventricular valve annulus such that the first one of the sections of the atrioventricular ring platform is configured to wind around the leaflets and gather together adjacent chordae of the subject's native atrioventricular valve to serve as a ventricular anchor for the atrioventricular ring platform.

7. The atrioventricular valve prosthesis according to claim 1, wherein the first one of the sections of the atrioventricular ring platform includes a first diameter, and the second section includes a second diameter that is smaller than the first diameter.

8. The atrioventricular valve prosthesis according to claim 1, wherein the third one of the sections of the atrioventricular ring platform comprises a diameter that is sized relative to the subject's native atrioventricular valve annulus such that the third one of the sections of the atrioventricular ring platform is configured to serve as an atrial anchor for the atrioventricular ring platform.

9. The atrioventricular valve prosthesis according to claim 1, wherein the valved-stent atrioventricular valve prosthetic device is balloon expandable.

10. An atrioventricular valve prosthesis according to claim 9, wherein the first one of the sections of the atrioventricular ring platform includes a first inner diameter in the deployed state, and the second section includes a second inner diameter in the deployed state, and wherein following expansion of the valved-stent atrioventricular valve prosthetic device to a third diameter, the atrioventricular ring platform provides a suitable size and dimension for subsequent implantation of the valved-stent atrioventricular valve prosthetic device by anchoring the valved-stent atrioventricular valve prosthetic device to at least one of the first inner diameter of the first one of the sections and the second inner diameter of the second one of the sections.

11. The atrioventricular valve prosthesis according to claim 1, wherein the valved-stent atrioventricular valve prosthetic device is self-expandable.

12. The atrioventricular valve prosthesis according to claim 1, wherein the atrioventricular ring platform and the valved-stent atrioventricular valve prosthetic device are configured for delivery by a transcatheter procedure.

* * * * *